United States Patent
Pathak et al.

[11] Patent Number: 6,027,446
[45] Date of Patent: Feb. 22, 2000

[54] PUBIC ARCH DETECTION AND INTERFERENCE ASSESSMENT IN TRANSRECTAL ULTRASOUND GUIDED PROSTATE CANCER THERAPY

[75] Inventors: Sayan D. Pathak; Peter D. Grimm; Yongmin Kim, all of Seattle, Wash.

[73] Assignee: Washington Univ. of Office of Technology Transfer, Seattle, Wash.

[21] Appl. No.: 09/187,830

[22] Filed: Nov. 6, 1998

Related U.S. Application Data

[60] Provisional application No. 60/071,129, Jan. 12, 1998.

[51] Int. Cl.[7] .......................................................... A61B 8/00
[52] U.S. Cl. ............................ 600/439; 600/443; 600/447
[58] Field of Search ....................................... 600/437, 439, 600/443, 449, 7, 1, 564, 566; 604/51, 59, 60–64; 607/97

[56] References Cited

U.S. PATENT DOCUMENTS

| | | | |
|---|---|---|---|
| 5,391,139 | 2/1995 | Edmundson | 600/7 |
| 5,443,069 | 8/1995 | Schaetzle | 600/439 |
| 5,471,988 | 12/1995 | Fujio et al. | 600/439 |
| 5,474,071 | 12/1995 | Chapelon et al. | 600/439 |
| 5,620,479 | 4/1997 | Diederich | 607/97 |
| 5,820,559 | 10/1998 | Ng et al. | 600/439 |
| 5,931,786 | 8/1999 | Whitemore, III et al. | 600/459 |
| 5,938,583 | 8/1999 | Grimm | 600/7 |

*Primary Examiner*—Marvin M. Lateef
*Assistant Examiner*—Ali M. Imam
*Attorney, Agent, or Firm*—Jensen & Puntigam, P.S.

[57] ABSTRACT

Transrectal ultrasound is used for accurate planning and targeting of placement of radioactive seeds by needles into the prostate in transperineal prostate brachytherapy. The pubic arch formed by the union of the pelvic bones is a potential barrier to passage of the needles containing the radioactive seeds. An initial image of the pubic arch is also provided by transrectal ultrasound, in addition to a transverse cross-sectional image of the prostate. The initial image of the pubic arch is processed using a technique to selectively enhance the contrast of the linear features of the edge of the ultrasound image. The enhanced image is then thresholded via the use of a percentile thresholding technique and then a curve modeling the shape of the pubic arch is fitted against the thresholded, enhanced image to produce a processed image of the pubic arch. This is then overlaid with the image of the prostate and a determination made as to pubic arch interference.

26 Claims, 5 Drawing Sheets

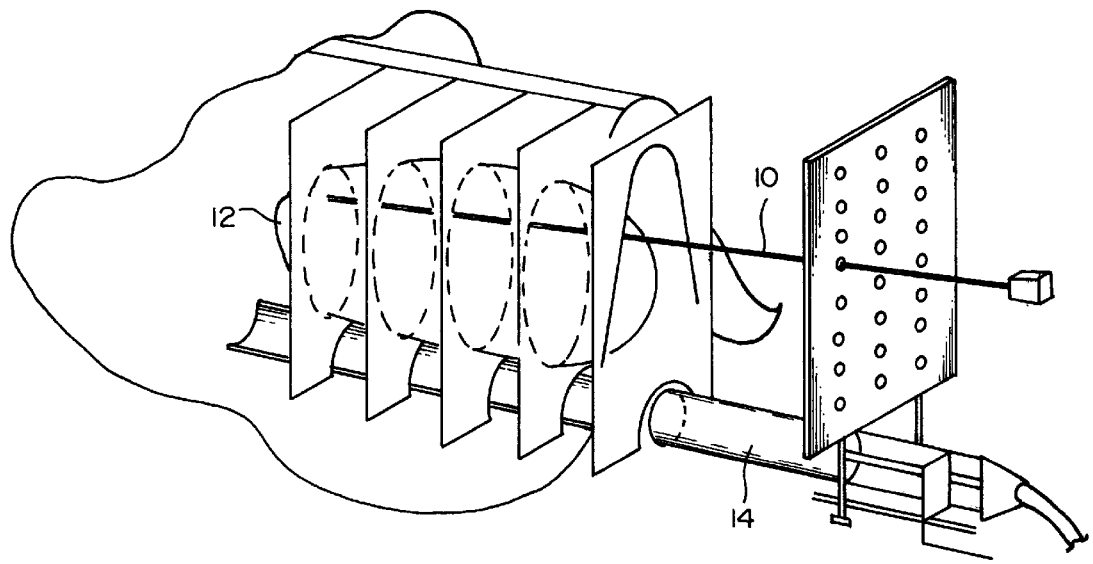
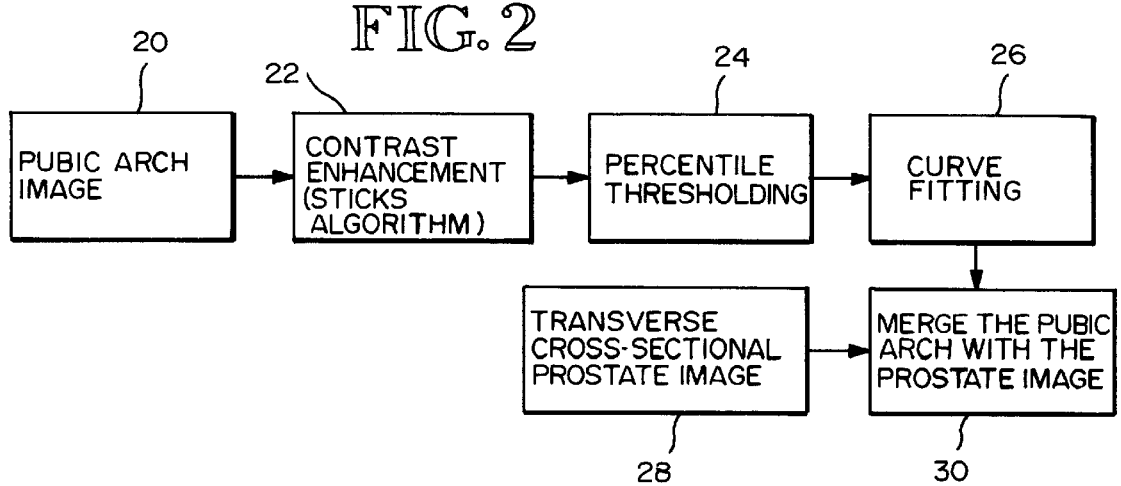

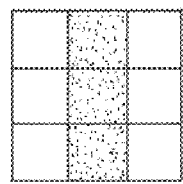 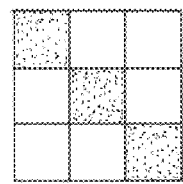 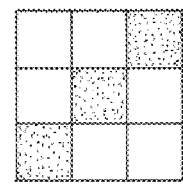 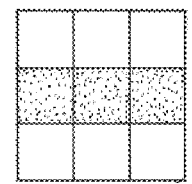
FIG.3A  FIG.3B  FIG.3C  FIG.3D
FIG.4A  FIG.4B  FIG.4C  FIG.4D
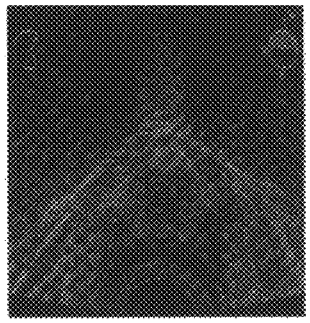 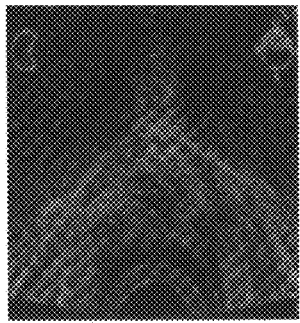 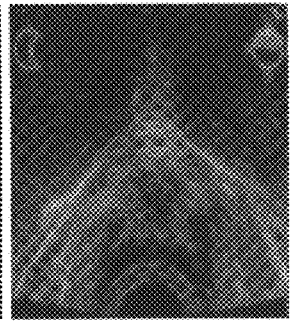 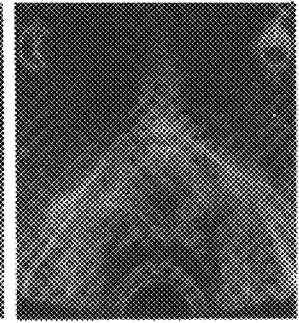

PUBIC ARCH DETECTION AND INTERFERENCE ASSESSMENT IN TRANSRECTAL ULTRASOUND GUIDED PROSTATE CANCER THERAPY

Priority of provisional application Ser. No. 60/071,129, filed on Jan. 12, 1998 is hereby claimed.

TECHNICAL FIELD

This invention relates generally to prostate brachytherapy (radioactive seed implantation), and more particularly concerns a method and system for determining pubic arch interference (PAI) in relation to the prostate gland.

BACKGROUND OF THE INVENTION

Adenocarcinoma of the prostate gland is the most frequently diagnosed cancer in men and remains the second leading cause of death in mature men. It is estimated that a man has a one in ten chance to develop prostate cancer. The reported incidence of prostate cancer has been increasing in the past ten years. The annual incidence of prostate cancer in the U.S. grew from 165,000 reported cases in 1993 to 318,000 reported cases in 1996. This increased incidence is believed to be primarily due to increased life expectancy, prostate specific antigen (PSA) screening, and improved diagnostic techniques, including transrectal ultrasound (TRUS). These factors have also lead to an increase in the number of younger men being diagnosed with localized prostate cancer. These trends are expected to continue.

The standard treatment regimens for prostate cancer are: (1) watchful waiting; (2) radical prostatectomy; (3) external beam radiation; and (4) prostate brachytherapy (radioactive seed implantation). Although "watchful waiting" is an appropriate choice for some men, the majority diagnosed with early stage prostate cancer will either request or require treatment of some kind. Radical prostatectomy is the "gold standard" for prostate cancer therapy, but is associated with significant morbidity, such as incontinence and impotence. While external beam radiation has proven to be an effective treatment, a long treatment time is usually required. The rising incidence of earlier stage prostate disease in younger patients with longer life expectancies has brought into focus both treatment effectiveness and the quality of life. The recent development of transperineal prostate brachytherapy as an effective treatment option has provided an alternative for patients seeking to preserve their prostate function as well as control the cancer.

Prostate brachytherapy, which can be performed as a single outpatient treatment, is recommended for patients with early stage (prostate-confined) disease. For patients with a high likelihood of disease located outside the prostate, it is often used as a "boost" following external beam radiation treatments. Because prostate brachytherapy is associated with a lower incidence of incontinence, impotence and rectal injury, it is emerging as a medically successful, cost-effective outpatient treatment in treating localized prostate cancer.

Prostate brachytherapy involves the accurate placement of radioactive materials, known as seeds, into the prostate gland according to a predetermined dosimetry plan. FIG. 1 shows a template-guided implant needle 10 inserted into the prostate gland 12 under the guidance of an ultrasound probe 14, which is inserted into the rectum of the patient. Successful execution of the brachytherapy procedure is the culmination of several specific steps. First, a prostate volume study using the transrectal ultrasound probe is performed. In the volume study, the patient lies on his back, the ultrasound probe is inserted into the rectum with the aid of a stabilizing/stepper apparatus and transverse cross-sectional images of the prostate are acquired at fixed interval, i.e. 5 mm, increments from the base (low point) of the gland to the apex thereof.

For each cross-sectional image obtained, the boundaries of the prostate are manually outlined by a technician. The overall volume of the prostate is determined using well-known step section planimetric techniques. The boundaries of the prostate obtained during the volume study not only result in an accurate determination of the size and shape of the prostate, but also provide important information for developing the dosimetry radiation plan. The end result of the computerized dosimetry plan is an accurate map for placing the seeds within the gland.

The basic brachytherapy technique is well known, and is described in detail in several publications, including several U.S. patents, including: An article by Grimm, Blasko, Ragde, Slyvester and Clarke, titled *Does Brachytherapy Have a Role in the Treatment of Prostate Cancer?*, Hematology/Oncology Clinics of North America, Vol. 10, No. 3, June 1996, and U.S. Pat. No. 5,626,829 titled: Method and Apparatus For Interstitial Radiation of the Prostate Gland.

The contents of the above publications are hereby incorporated by reference. A second important step in preoperative evaluation for possible use of brachytherapy is the determination of pubic arch interference, referred to as PAI. The pubic bones meet centrally in the pelvis, and viewed from the perineum, they form an arch. The prostate is positioned behind this arch (again, as viewed from the perineum). In order for the seed implantation technique to be successful, the implant needles must be able to pass within the area between (interior of) the arch into the prostate gland. Significant pubic arch interference occurs when an arch is too narrow (or the prostate too large) to allow the passage of the implantation needles in many places. PAI may occur with both large and small prostate glands. However, typically in a normal sized male, PAI is rarely encountered when the prostate volume is less than 40 cc. When the prostate gland is above 60 cc, PAI is almost always encountered, and such patients first undergo either prostate shrinkage with hormones or select another form of treatment.

While the ultrasound probe can produce an accurate estimation of gland volume, it is unable to predict the position of the pubic arch. The current evaluation process requires that PAI be assessed using a separate CT examination, which is typically referred to as a "correlate" CT scan. In the CT scan, the position of the pubic arch in relation to the prostate is determined by outlining the prostate gland at its widest transverse cross-sectional dimension and superimposing this outline on the image of the pubic arch produced by the CT scan. Currently, clinicians use the rule of thumb of "more than one-fourth PIA" to determine whether a person can receive the seed implants, i.e. if the pubic arch covers more than one-fourth of the prostate gland, the technique is not used.

The correlate CT scan, however, while helpful to the clinician, is expensive and time-consuming. Not only is the scan itself expensive, but because patients are often initially prescheduled with a radiologist for a correlate CT scan, many of which are canceled following determination from the volume study that a particular prostate gland has a greater volume than 60 cc or smaller than 40 cc, a valuable time slot for the radiologist which could have been used for another patient is typically lost.

Further, because the position of the patient in the prostate brachytherapy procedure cannot be simulated in the CT scan machine due to inadequate space in the CT machine, the correlate CT scan can provide only a rough guideline of the actual configuration of the pubic arch. Hence, the determination of PAI using a CT scan is less accurate than is desirable and adds significantly to the overall expense of the brachytherapy treatment.

It is critical that PAI be accurately determined, as the brachytherapist will be forced to use a different template hole and to insert the needle at an angle to get past the pubic arch and to implant the seed as near to the target dosimetry position as possible if pubic arch interference is encountered during the brachytherapy procedure which was not determined by the initial pubic arch interference process. In prostate brachytherapy, there is only one opportunity to place the seeds correctly within the prostate, as the seeds which are implanted remain in the patient and cannot be removed. Hence, any obstruction problems caused by the pubic arch must be known prior to the seed implant procedure. While one or two needle insertions that deviate from the preplanned implant pattern will not typically affect the dose distribution, more than four obstructions/deviations are likely to affect the seed distribution and the optimal dose delivered to the prostate gland.

Hence, it is quite desirable that an accurate PAI assessment be made prior to beginning the seed implant procedure; it is also desirable to reduce the present cost of this part of the procedure.

DISCLOSURE OF THE INVENTION

Accordingly, the present invention includes a method for determining pubic arch interference relative to the prostate gland of a patient using an ultrasound machine, comprising the steps of: acquiring an initial ultrasound image of the pubic arch; acquiring an ultrasound image of a transverse cross-sectional outline of the prostate gland; outlining the approximate shape of the pubic arch from the initial ultrasound image thereof; and merging the outline of the pubic arch with the transverse cross-sectional image of the prostate to determine interference between the pubic arch and the prostate gland.

Another aspect of the present invention is a system for determining pubic arch interference relative to the prostate gland of a patient, comprising: a single means for producing an initial ultrasound image of the pubic arch of a patient and also for producing an ultrasound image of a transverse cross-sectional outline of the prostate of the patient; means for processing the initial ultrasound image of the pubic arch to produce a substantially accurate image thereof; and means for merging the processed image of the pubic arch with the transverse cross-sectional image of the prostate to determine interference between the pubic arch and the prostate gland.

BRIEF DESCRIPTION OF THE DRAWINGS

FIG. 1 is a schematic view illustrating the prostate brachytherapy procedure.

FIG. 2 is a simple flow chart showing the steps in processing of the initial pubic arch image obtained by an ultrasound probe.

FIGS. 3A–3D are a series of diagrams showing the edge enhancement technique used in the method of the present invention.

FIGS. 4A–4D are a series of images showing the results of several variations of one step of the method of the present invention.

BEST MODE FOR CARRYING OUT THE INVENTION

The ultrasound probe 14 which is used to obtain transverse cross-sectional images of the prostate during the initial prostate volume study (FIG. 1) is also capable of producing an image of the patient's pubic arch at the same time. However, while the ultrasound probe provides an excellent image of the prostatic scoma (the surrounding and supporting tissue), the visibility of the pubic bones themselves in relation to the pelvic outlet is typically poor. The images of the pubic arch are poorly defined typically for the following reasons: (1) the pelvic musculature and rectal wall generate strong echoes while results in linear artifacts in the pubic arch images, which give the false appearance of a pubic bone; (2) fenestras (i.e. small openings) present in the pelvis tend to scatter the incident ultrasound energy in random directions, producing artifacts, such as missing edges; (3) the pubic arch is positioned at considerable distance from the ultrasound probe and, hence, greater attenuation of the ultrasound energy results in poor contrast for the pubic arch; and (4) the edge information of the pelvic bones located in the far field of the ultrasound image is degraded due to excessive interpolation of the pre-scan converted data.

In the present invention, the previously-used CT correlate scan to produce the PAI is eliminated, and the initial image produced by the ultrasound probe is automatically processed in a series of steps to create an accurate image of the pubic arch (referred to as a detected image) and then overlaying the detected image of the pubic arch relative to the transverse cross-section of the prostate.

Ultrasound image acquiring apparatus is well known. An example of such an apparatus is shown in U.S. Pat. No. 5,795,296 issued on Aug. 18, 1998. Such a system will typically include a conventional ultrasound transducer array, a transmitter/receiver for the ultrasound signals, a system controller for receiving and displaying user control information via a user interface device, and processing capability for processing the raw data and producing the basic ultrasound images.

Figure 5A:
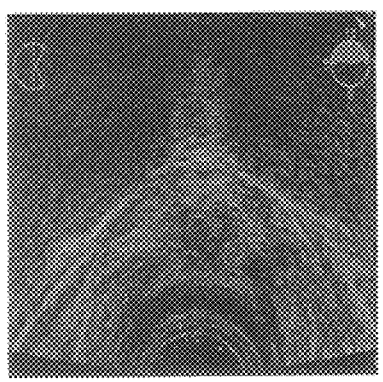
FIGS. 5A–5F are a series of images showing the sequence of steps of the method of the present invention.
Figure 5B:
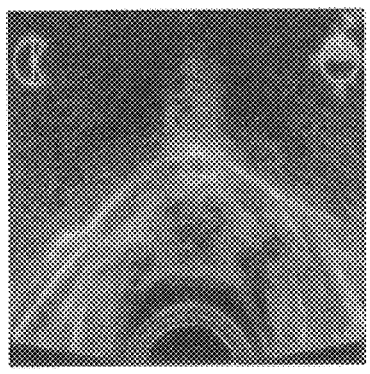

Referring to FIG. 2 relative to the sequence of steps in the processing of the pubic arch image, the original image of the pubic arch is provided by the ultrasound probe. This is shown as block 20 in the diagram of FIG. 2 and is also shown in FIGS. 4A and 5A. The image of the pubic arch is then processed to develop an outline of the arch. In a first processing step, the ultrasound image of the pubic arch, in particular the edges thereof, are enhanced by a line "segmenting" technique. Conventional methods of segmenting a particular image by identifying its edges are based on detecting step discontinuities. In some cases, angular information of an edge is used by calculating the angle from the immediate neighborhood (location) of a particular pixel in the image.

With ultrasound images, however, such conventional approaches are not appropriate due to the poor signal to noise ratio of the ultrasound signal, as well as speckle noises. Also, when conventional edge detection algorithms are applied to detect edges of ultrasound images, they generate an excessive number of false edges. In the present invention, edge detection using a linear structure segmentation approach is used as opposed to a step discontinuity approach. Using segments with different possible angular orientations in each neighborhood as a template, selecting one orientation that is most likely to represent a line in the image results in reduction of speckle noise and improved edge information for ultrasound images.

The segmentation technique for enhancing ultrasound images is well known, and is discussed in an article by Czerwinski, Jones and O'Brien, Jr., titled "Edge Detection in Ultrasound Speckle Noise" in the Proceedings of the IEEE International Conference on Image Processing, Vol. 3, pp. 304–308 (November 1994), which is incorporated by reference herein. In a simple summary, a linear structure segmentation/contrast enhancement technique is used as a first step in the processing of the ultrasound-generated pubic arch image. In the flow chart of FIG. 2, the initial pubic arch image provided by the ultrasound probe is shown at block 20, while the edge enhancement provided by linear structure segmentation/contrast enhancement processing is shown at block 22.

The contrast-enhanced image from block 22 is then processed with a threshold by a technique called percentile thresholding, which reduces the noise present in the contrast-enhanced pubic arch image. This is shown in block 24. A selected curve, such as a parabola, is then applied against the image, as indicated in block 26. Following the comparison of the thresholded image with the curve, the final detected, i.e. processed, image is compared or "merged" with the transverse cross-sectional image of the prostate (block 28) by means of overlaying the images, the two images being simultaneously displayed, which permits the determination of PAI by examining the position of the overlayed processed pubic arch image relative to the prostate image, as indicated in block 30.

Figure 8A:
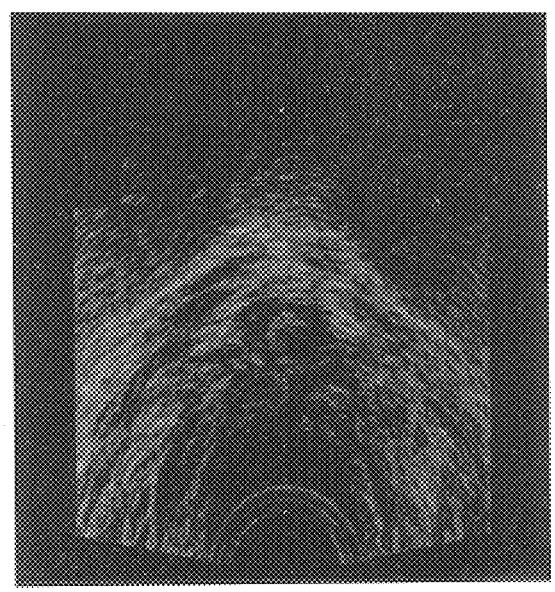
FIGS. 8A and 8B are two ultrasound images showing the manual outlining of a pubic arch.
Figure 8B:
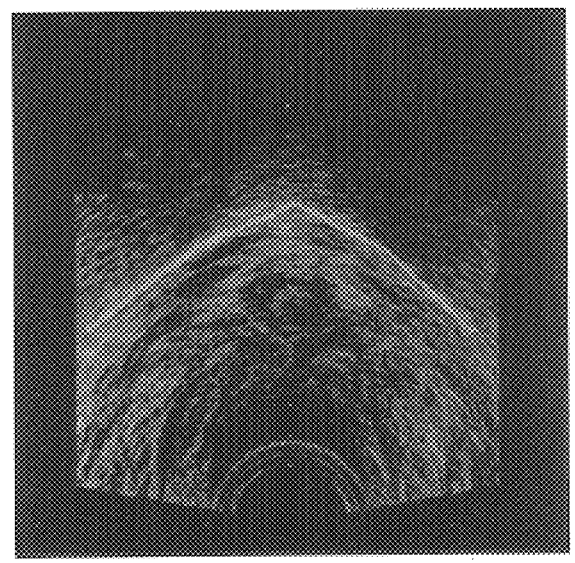

As a possible alternative to the above automatic processing sequence, the ultrasound image of the pubic arch can first be divided into successive segments manually, such as on the screen, by an operator who distinguishes the image of the arch from the rest of the image information. The operator will move a boundary drawing tool (mouse) to a selected starting point on the image and will then move the mouse to successive points on the ultrasound image. A line will be drawn between each successive point in turn. An electrical signal is generated in response to action of the mouse tool to outline the arch. Such drawing tools for ultrasound images are will known. Typically, five or six selected points will be sufficient to outline the arch. FIGS. 8A and 8B show an initial ultrasound image and the image with a manually outlined pubic arch. The segmented image may then be smoothed to provide a continuous final image which can be compared with the prostate image.

The "merger" of the ultrasound image of the pubic arch with the ultrasound image of the prostate, in order to determine pubic arch interference, can be done by placing the two images together on the screen, one over the other, or by automatic comparison of the two images to determine extent of overlap. The words "merger" and "overlap" of the images are intended to cover both possibilities.

Referring now to the automatic processing sequence (FIG. 2) of the original (ultrasound) pubic arch image in more detail, the initial step is, as indicated above, contrast enhancement of the initial image, particularly the edges of the pubic arch. The pubic arch is generally a linear structure which can be described as comprised of several short, successive linear segments ("sticks"). In order to simulate the pubic arch by a set of short line segments, Bayesian decision theory is used to select the most powerful line segment out of a defined set of line segments for each successive portion or location in the pubic arch image. Bayesian decision theory is well known, and is described in a number of different publications, among them being the above-mentioned article to Czerwinski et al and a book by H. B. Poor, titled "An Introduction to Signal Detection and Estimation," NY (Springer-Verlag) 1988.

FIG. 3 illustrates, in a single 3×3 pixel image location or neighborhood, four possible line segment configurations. For each such location, only one segment will best describe the linear segment of the image in that particular location. According to Bayesian decision theory, given that an event x occurs, a decision rule is selected which minimizes the risk (incorrectness) of the decision. In a small region of the image identified as kernel space [Ω(N)], where N is the width and height of the region (e.g., N=3 in FIG. 3), the set Ω is partitioned into 2N−2=M different states described by $\omega_i$, $\forall i=1 \ldots M$, with each state ($\omega_i$) representing one particular orientation (of the four shown in FIG. 3) of a line segment in Ω.

Now, let x be probabilistic in nature, representing a manifestation of M different states, and assume that the conditional probability of observing x, given $\omega_i$, is known to the observer.

Based on x and the desired function [d(·)], the estimated state of nature is $\omega_j$. Ideally, $\omega_j=\omega_i$, $\forall i=j$, i.e. the estimated state of nature agrees with the true state of nature. However, if $\omega_j=\omega_i$, $\forall i\neq j$, then an error is present and those errors are penalized by assigning each error a selected cost value. Let the matrix c($c_{ij}$ $\forall i,j=1 \ldots M$) be the cost associated with making a decision. Using Bayes' rule, the risk R is defined as the sum of products between all costs and the corresponding probabilities as:

$$R = \sum_{i=1}^{M} \sum_{j=1}^{M} C_{ij} P[\omega_j \mid x] \qquad (1)$$

We minimize the risk R by minimizing Equation (1). When a cost matrix where zeros represent correct decisions and ones represent incorrect decisions, the above Equation (1) can be written as:

$$R = \sum_{i=1}^{M} \sum_{j \neq 1}^{M} P[\omega_j \mid x] = 1 - \sum_{i=1}^{M} P[\omega_i \mid x] \qquad (2)$$

Applying Bayes' rule to Equation (2), the expression $P[\omega_i|x]$ $xP[x|\omega_i] \cdot P[\omega_i]$ where $P[\omega_i]$ is the prior probability of the state $i^{th}$ the optimum decision in this case, assuming that the prior probabilities are unknown, is equivalent to:

$$\max P[x|\omega_i] \forall i \qquad (3)$$

Moreover, we define the $i^{th}$ hypothesis ($H_i$) as the line template in the $i^{th}$ orientation represented by the state $\omega_i$.

When x is observed in a particular location, it is possible to apply the maximum likelihood test (MLT) on Equation (3) in order to select the hypothesis that most likely describes x. It can be shown that using the cost function defined above, that the hypothesis with the maximum sum of gray values along its path satisfies MLT. This sum obtained along the orientation of the line element corresponding to the hypothesis which satisfies MLT is the most probable description of a line segment in $\Omega(N)$. In a given location, the sum obtained when an edge is present is higher than the sum obtained when no edge is present.

The final image is obtained by scaling the sums from 0 to the maximum allowable pixel value in the image, which in the present case is 255. This scaling makes the edge pixels have a relatively high gray value, while the non-edge pixels have a lower gray value. When two or more line elements in a location satisfy MLT, the sum of the pixels computed along the line elements is the same, which indicates that all of the elements that satisfy MLT are equally likely to occur in that particular location.

A short line segment representation of the image results in numerous missing edges and less reduction in speckle noises compared to the results obtained with longer line segments. FIGS. 4A–4D illustrate that as the length of the line segments increase, the detection of large-scale linear features is improved, while speckle noise decorrelated over a large distance drop out. However, large line segments cause an increase in false edge detection. Since it is desirable to reduce the speckles in the image but at the same time improve the contrast of the image as a first step toward accurately detecting the pubic arch, an intermediate line segment length of 15 pixels, has been selected. FIG. 4A shows the original image, while FIGS. 4B, 4C and 4D show the original image processed with line segment lengths of 7, 15 and 21 pixels, respectively.

Enhancement of contrast of the pubic arch in the ultrasound image using a line segment process provides better results than the traditional methods of enhancing image contrasts, such as via histogram equalization, for instance. However, there still exists a substantial amount of noise in the line segment-enhanced pubic arch image of FIG. 4C which should be suppressed in order to better identify the pubic arch.

Figure 5C:
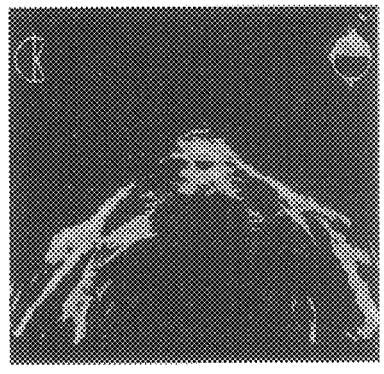

An automatic thresholding process is next used to identify the pixels that could represent the pubic bones. A threshold value is determined that will result in the suppression of false edges while retaining the true edges of the pubic arch. The cumulative distributive function (cdf) corresponding to the normalized histogram of an image is defined as:

$$Pcum(k) = \sum_{i=0}^{k} p(i) \quad (4)$$

where P(i) is the probability density function obtained from the histogram and k varies from 0 to 255. It is assumed that in the ultrasound pubic arch image, f% of the pixels represent pubic bones while the rest are tissue pixels and others. The threshold (thresh) is calculated automatically for every image such that $P_{cum}(thresh) \geq 1-f/100$ is satisfied. All the pixel values equal to or greater than the "thresh" value are labeled as bone. This procedure is referred to as percentile thresholding. The value of f is calculated on the original ultrasound image. In the present invention, a value of f of 10 is used, which was determined empirically by manually labeling the pubic arch area in actual known test images and calculating the percentage of this area within the pubic arch area compared to the area of the entire image. The result of the percentile thresholding processing is shown in FIG. 5C, with the white pixels therein being the ones labeled as bone.

A "least squares" curve fitting step, such as with a parabolic curve, is next used with the thresholded-enhanced image, i.e. f(x,y)=0, where x and y are coordinates of those points which lie on the curve. As seen in FIG. 5C, some of those points are labeled incorrectly due to the overlap in the gray areas of the bone and soft tissue, typically near the apex of the prostate. This results in an error in fitting, referred to as $e_{fit}$, between the points labeled as bone by the percentile thresholding process and the corresponding points on the curve (a parabola in this case), as shown in FIG. 6D.

Figure 5D:
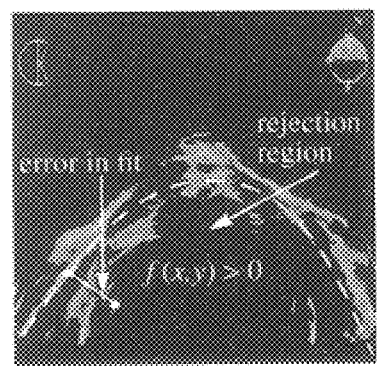
Figure 5E:
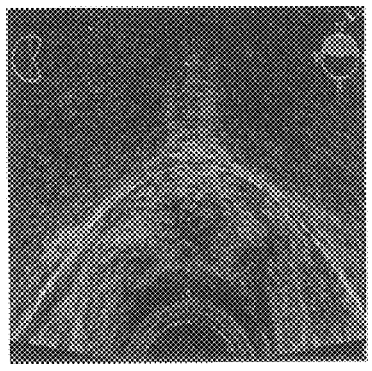
Figure 5F:
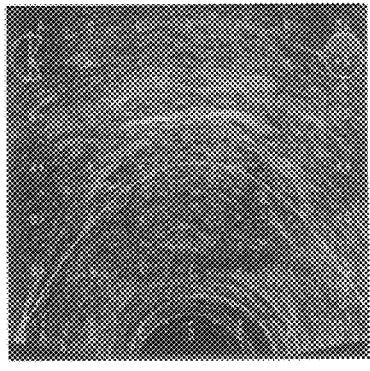

The $e_{fit}$ value is calculated by adding the error in the curve fit for all the points labeled as bone. The $e_{fit}$ value originates primarily from an incorrect labeling of the rectal wall and pelvic musculature as bone, typically due to the strong echoes from those areas. These points all lie in the rejection region relative to the curve fit, i.e. $f_x(x,y)>0$, the area shown in FIG. 5D. All of those points in the rejection region are then removed from those points which have been previously labeled as bone after the percentile thresholding process. The curve is then "fitted" once again, and $e_{fit}$ is again calculated. Since most of the ultrasound energy incident on the bone is reflected due to its high acoustic impedance, the curve obtained in the second pass after rejecting the original falsely labeled points in the region of f(x,y)>0 will result in better identification of the actual pubic arch. The curve fitting processing is repeated several times, typically until the $e_{fit}$ value falls below 1 mm, which is approximately the diameter of the implant needle used in prostate brachytherapy.

At this point, the basic processing of the ultrasound image of the pubic arch is completed. This final image of the pubic arch is referred to herein as the detected or processed image.

Figure 9:
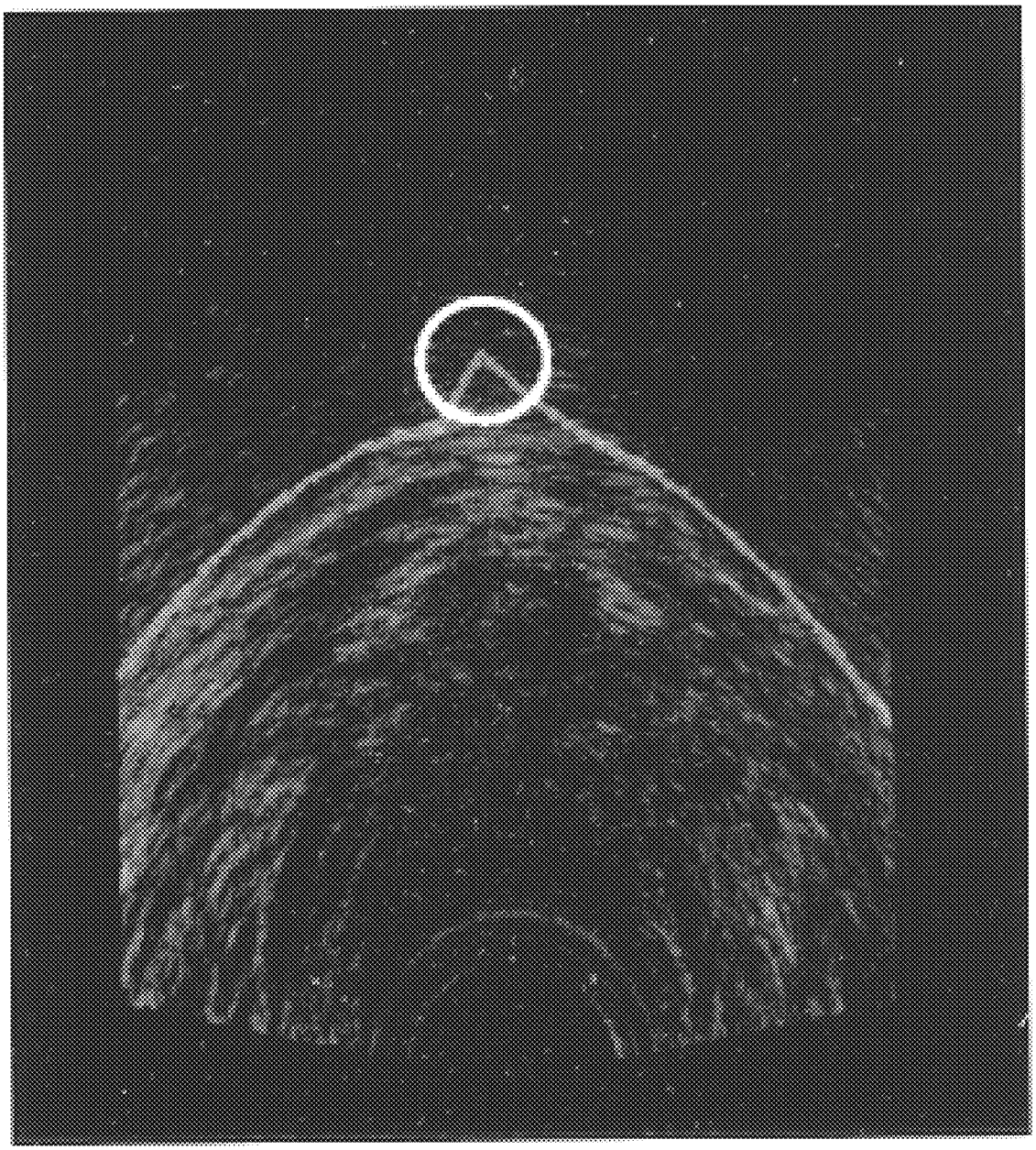
FIG. 9 is an ultrasound image showing a manual editing step for a previously automatically processed pubic arch image.

The detailed (processed) image may be manually edited using known image adjustment tools. The whole curve may be moved, i.e. repositioned, by selecting the proper mode and moving the mouse to the boundary. The mouse is then clicked and held and then the boundary is moved to the desired location. The curve is moved without changing its shape. Different portions of the outlined arch may also be changed. The mouse is moved to the area of the boundary to be changed. The mouse is then clicked and held while moving it to the desired location, at which point it is released, and the revised boundary exists. Revision of a portion of a boundary is shown in FIG. 9.

Figure 7A:
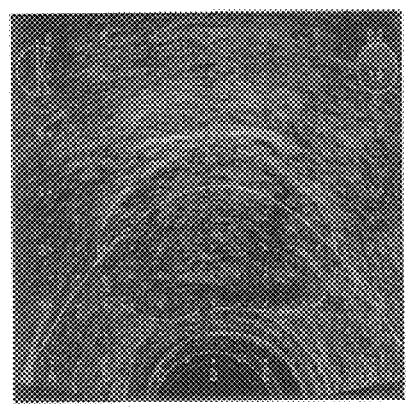
FIGS. 7A and 7B are two images showing an overlay of a pubic arch and a prostate gland of two different patients.
Figure 7B:
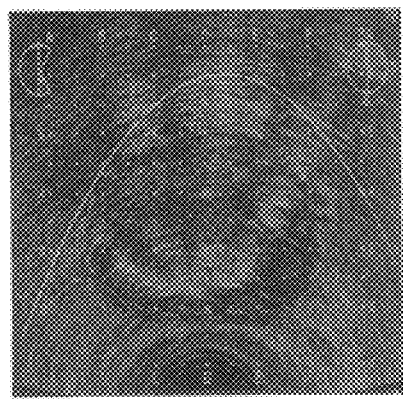

In the next step, the processed image of the pubic arch is projected onto the transverse cross-sectional image of the prostate in order to determine PAI. FIGS. 7A and 7B show two cases involving an automatically detected pubic arch (solid line 31) and a cross-section image of the prostate for two patients, the boundary of the prostate in each case indicated by a dashed line 32. FIG. 7A shows a case where a significant part of the prostate is located above the pubic arch, which indicates the presence of PAI. The seed implant technique would not be performed in such a situation. FIG. 7B shows a patient where no part of the prostate is located above the detected pubic arch, thus indicating the absence of PAI, and thus a successful candidate for the seed implant technique.

The above-described PAI technique has been evaluated experimentally. In the experimental protocol, the initial ultrasound-unenhanced pubic arch image and cross-sectional images of the prostate were obtained. The pubic arch image-enhancing process was followed as described above, and then the processed, i.e. detected, pubic arch image was overlaid on top of the transverse cross-sectional image of the prostate. Then, the actual seed implant procedure was carried out at each of the individual grid points (a total of 20) set out in FIG. 6, which are all located near the detected pubic arch.

In the implant procedure, 100 or more seeds are placed in the prostate using a template under the guidance of the ultrasound probe. In pursuing the above experimental protocol, it was assumed that the position of the pelvis of the patient during the seed implant procedure is in fact identical to that during the pre-seed implant volume study. As shown in FIG. 1, the prostate is positioned within the dome-like pelvis, while the pubic arch forms a door onto the dome. Inside the fitted curve (the detected pubic arch, where f(x,y)>0) is the soft tissue through which seeds can be implanted.

Figure 6:
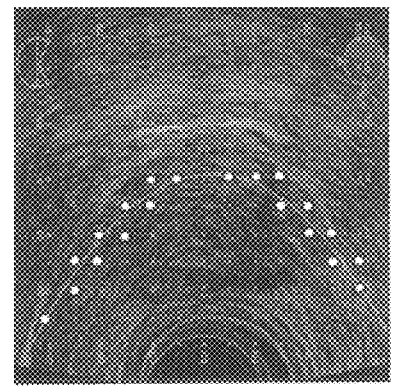
FIG. 6 is an image showing an overlay of a prostate cross-sectional image and a brachytherapy template.

The remaining region represents the zone where a needle cannot be inserted due to the presence of the pelvic bone. The predictions at the various grid points of FIG. 6 are compared against the corresponding actual experimental results. If a particular position is predicted to be either a bone or soft tissue, based on the pubic arch detection process, the experimental result may confirm it; or on the other hand, the two may disagree. The procedure is repeated at all of the grid points set forth in FIG. 6.

The mean success rate of such experimental results has been documented to be 90%, which indicates that the process of the present invention on the average predicts the location of the pubic arch relative to the prostate correctly for approximately 18 out of the 20 grid points set forth in FIG. 6. The mean error rate of the present process in predicting soft tissue which in fact is bone is approximately 4%. This small error rate is clinically satisfactory, and is at least as good as that achieved by present CT scan results.

It is generally accepted that for a successful brachytherapy procedure, the needle obstructions produced by the pubic arch relative to the prostate should not exceed four per patient, since, as indicated above, more obstructions than four could significantly increase the risk of a poor dosimetry effect. The error in predicting PAI with the present system is quite minimal, as discussed above; the actual errors can be overcome at the time of the seed implant procedure by proper action of the therapist. Hence, experimental results have indicated that the present invention has an error rate which is well within acceptable limits and can in fact be used clinically to assess PAI.

The above described processing sequence can be carried out in an external computer that has a frame grabber to digitize the images or within the ultrasound machine itself. When the above-described processing is accomplished on an external PC-based workstation which has a link to the ultrasound machine (such as shown in the '296 patent referenced above) which digitizes the ultrasound video output from the ultrasound probe, PAI assessment can be made interactively during pre-seed implant volume study sessions. The processing can also be carried out in the ultrasound machine itself if it incorporates programmable computing capabilities, which could eliminate the need for an external computer. With this interactive pubic arch detection capability, misalignment between the pubic arch and the central axis of the ultrasound image can be easily detected during the pre-seed implant volume study, enabling the operator to reposition the pelvis to align the pubic arch and the prostate before proceeding.

The determination of pubic arch interference in patients undergoing prostate brachytherapy is a critical part of the overall brachytherapy procedure and as indicated above is currently determined with a CT scan. However, the CT scan is known to be inexact, time consuming and expensive. The above-identified process permits identification of PAI using the ultrasound probe which determines the initial volume of the prostate, with little additional time and effort. The present invention combines a processed ultrasound image of the pubic arch image with the ultrasound image of the prostate at its largest transverse cross-sectional dimension. The system predicts the presence of bone or soft tissue in the vicinity of the pubic arch with 90% accuracy. The error in predicting PAI is determined to be within clinically acceptable limits. Improved accuracy in predicting PAI can be achieved by aligning the transverse cross-sectional image of the prostate and the pubic arch with the central axis of the ultrasound images.

Although a preferred embodiment of the invention has been disclosed herein for illustration, it should be understood that various changes, modifications and substitutions may be incorporated in such embodiment without departing from the spirit of the invention, which is defined by the claims as follows.

What is claimed is:

1. A method for determining pubic arch interference relative to the prostate gland of a patient, comprising the steps of:

acquiring an initial ultrasound image of the pubic arch;

acquiring an ultrasound image of a transverse cross-sectional outline of the prostate;

outlining the approximate true shape of the pubic arch from the initial ultrasound image thereof; and merging the outline of the pubic arch with the transverse cross-sectional image of the prostate to determine pubic arch interference.

2. A method of claim 1 wherein the step of outlining the pubic arch includes the step of segmenting the ultrasound image of the pubic arch.

3. A method of claim 1, wherein the step of outlining the pubic arch is carried out automatically.

4. A method of claim 3, wherein the step of automatic outlining includes the steps of generating line segments delineating the pubic arch and smoothing said line segments to achieve a smooth outline of the pubic arch.

5. A method of claim 3, wherein the step of outlining the pubic arch includes the steps of edge detecting the initial ultrasound image of the pubic arch, thresholding the edge-detected image, comparing the thresholded image with a curved model of a pubic arch, and discarding selected portions of the thresholded image which are outside a selected difference range relative to the curve to produce a processed image of the pubic arch.

6. A method of claim 5, wherein the step of edge detecting includes enhancing the pubic arch edge using successive line segments, each line segment having one of a selected plurality of different orientations, the one orientation at each location along the pubic arch being most likely to represent the pubic arch at that location.

7. A method of claim 5, wherein the threshold value is $\geq 1-f/100$, wherein f is approximately 10 and wherein all pixel values at least meeting the threshold value are designated as bone.

8. A method of claim 5, wherein the step of comparing is repeated until there are no portions of the threshold image outside of the selected difference range.

9. A method of claim 1, wherein the public arch interference is determined with an accuracy greater than 90%.

10. A method of claim 1, wherein the initial ultrasound image of the pubic arch is stored in memory in the ultrasound machine and the step of automatically outlining the pubic arch is carried out in the ultrasound machine.

11. A method of claim 1 wherein the initial ultrasound image of the pubic arch is stored in an external computer and the step of automatically outlining the pubic arch is carried out in the external computer.

12. A method of claim 1, wherein the step of outlining the pubic arch is carried out manually by an operator.

13. A method of claim 12, wherein the step of outlining includes the step of generating an electrical signal corresponding to the outlining of the arch by the operator from the actual ultrasound image of the pubic arch.

14. A method of claim 1, wherein the initial ultrasound image of the prostate and the initial ultrasound image of the pubic arch are obtained by transrectal ultrasound during a single procedure.

15. A method of claim 3, including the step of manually editing the true shape outline of the pubic arch.

16. A method of claim 15, wherein the step of manual editing includes at least one of the following: a) moving the entire true shape outline without changing its shape and b) changing the shape of selected portions of the true shape outline.

17. A method for determining whether the pubic arch of a patient interferes with access in a prostate gland of a patient, comprising the steps of:

displaying an initial ultrasound image of the pubic arch;

outlining the approximate true shape of the pubic arch from the initial ultrasound image; and merging and displaying the outline of the pubic arch with a transverse cross-sectional ultrasound image of the prostate gland of the patient to determine pubic arch interference.

18. A system for determining pubic arch interference relative to the prostate gland of a patient, comprising:

means for producing an initial ultrasound image of the pubic arch of the patient and for producing an ultrasound image of a transverse cross-sectional outline of the prostate of the patient;

means for processing the initial ultrasound image of the pubic arch to produce a substantially accurate image thereof; and means for merging the processed image of the pubic arch with the transverse cross-sectional image of the prostate to determine pubic arch interference.

19. A system of claim 15, wherein the processing means includes means for comparing a partially processed image, edge enhanced and thresholded, with a curve resembling a typical pubic arch and means for discarding selected portions of the partially processed image which are outside a selected difference range relative to the curve.

20. A system of claim 18, wherein pubic arch interference is determined with an accuracy of at least 90%.

21. A system of claim 18, wherein the producing means is an ultrasound machine.

22. A system of claim 21, wherein the initial ultrasound image of the pubic arch is stored in memory of an ultrasound machine and processed in the ultrasound machine.

23. A system of claim 21, wherein the initial ultrasound image of the pubic arch is stored in memory in an external computer and processed in the external computer.

24. A method for determining whether pubic arch of a patient interferes with access to a prostate gland of the patient for prostate brachytherapy treatment, the method comprising the steps of:

inserting an ultrasound probe into the rectum of the patient;

acquiring an initial ultrasound image of the pubic arch by the ultrasound probe;

acquiring an ultrasound image of a transverse cross-section of the prostate bland by the ultrasound probe;

outlining the approximate true shape of the pubic arch from the initial ultrasound image;

merging the outline of the pubic arch with the transverse cross-sectional image of the prostate gland to determine pubic arch interference; and inserting a plurality of needles into the prostate gland under the guidance of the ultrasound probe when the pubic arch is determined not to interfere with access to the prostate gland.

25. The method of claim 24, wherein the steps of acquiring the initial ultrasound image and acquiring the prostate gland cross-section ultrasound image are performed by an ultrasound machine and further comprise the steps of displaying the acquired initial ultrasound image and displaying the acquired prostate gland cross-section ultrasound image; in which the steps of displaying the acquired initial ultrasound image, displaying the acquired prostate gland cross-section ultrasound image, outlining the approximate true shape of the pubic arch, and merging the outline of the pubic arch with the transverse cross-sectional image of the prostate gland are performed on an external computer.

26. The method of claim 24, wherein the steps of acquiring the initial ultrasound image, acquiring the prostate gland cross-section ultrasound image, outlining the approximate true shape of the pubic arch, and merging the outline of the pubic arch with the transverse cross-sectional image of the prostate gland are performed by an ultrasound machine.

* * * * *